(12) United States Patent
Borchert et al.

(10) Patent No.: US 6,368,805 B1
(45) Date of Patent: Apr. 9, 2002

(54) METHODS OF PRODUCING POLYNUCLEOTIDE VARIANTS

(75) Inventors: Torben Vedel Borchert, Østerbro (DK); Titus Kretzschmar, Munich (DE); Joel R. Cherry, Davis, CA (US); Vind Jesper, Værløse (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/644,953

(22) Filed: Aug. 23, 2000

Related U.S. Application Data

(63) Continuation of application No. 09/040,698, filed on Mar. 18, 1998, now Pat. No. 6,159,688.
(60) Provisional application No. 60/044,944, filed on Apr. 25, 1997, and provisional application No. 60/050,632, filed on Jun. 24, 1997.

(30) Foreign Application Priority Data

| Mar. 18, 1997 | (DK) | ................................. 0306/97 |
| Apr. 17, 1997 | (DK) | ................................. 0433/97 |
| May 30, 1997 | (DK) | ................................. 0623/97 |

(51) Int. Cl.⁷ ......................... C12Q 1/68; C12P 19/34; C12N 15/00; C12N 15/63
(52) U.S. Cl. ............... 435/6; 435/91.2; 435/440; 435/471; 435/455; 435/468
(58) Field of Search ................... 435/6, 91.2, 440, 435/455, 468, 471

(56) References Cited

U.S. PATENT DOCUMENTS

| 4,518,584 A | 5/1985 | Mark et al. ............. 424/85 |
| 4,894,331 A | 1/1990 | Ratzkin et al. .......... 435/94 |
| 5,093,257 A | 3/1992 | Gray ................... 435/202 |
| 5,830,696 A | 11/1998 | Short ................. 435/69.1 |
| 5,939,250 A | 8/1999 | Short .................... 435/4 |
| 5,958,672 A | 9/1999 | Short .................... 435/4 |
| 5,965,408 A | 10/1999 | Short ................. 435/91.1 |
| 6,001,574 A | 12/1999 | Short et al. ............. 435/6 |
| 6,004,788 A | 12/1999 | Short .................. 435/183 |
| 6,030,779 A | 2/2000 | Short .................... 435/6 |
| 6,054,267 A | 4/2000 | Short .................... 435/6 |
| 6,057,103 A | 5/2000 | Short .................... 435/6 |
| 6,096,548 A | * 8/2000 | Stemmer ............... 435/440 |
| 6,117,679 A | 9/2000 | Stemmer ............... 435/440 |
| 6,132,970 A | 10/2000 | Stemmer ................. 435/6 |
| 6,153,410 A | 11/2000 | Arnold et al. ......... 435/91.2 |
| 6,165,793 A | 12/2000 | Stemmer ............... 435/440 |
| 6,168,919 B1 | 1/2001 | Short .................... 435/6 |
| 6,171,820 B1 | 1/2001 | Short ................. 435/69.1 |
| 6,174,673 B1 | 1/2001 | Short et al. ............. 435/6 |
| 6,177,263 B1 | 1/2001 | Arnold et al. ......... 435/91.1 |
| 6,180,406 B1 | 1/2001 | Stemmer ............... 435/440 |

FOREIGN PATENT DOCUMENTS

| WO | WO 93/01285 | 1/1993 |
| WO | WO 95/17413 | 6/1995 |
| WO | WO 95/22625 | 8/1995 |
| WO | WO 97/07205 | 2/1997 |
| WO | WO 97/35966 | 10/1997 |
| WO | WO 98/42832 | 10/1998 |

OTHER PUBLICATIONS

Crameri et al., Nature, vol. 391, pp. 288–291 (Jan. 15, 1998).
Stemmer, Nature, vol. 370, No. 4, pp. 389–391 (Aug. 4, 1994).
Stemmer, Proc. Natl. Acad. Sci., vol. 91, pp. 10747–10751 (Oct. 1994).
Weber et al., Nucleic Acids Research, vol. 11, No. 16 pp. 5561–5669, (1983).
Pompon et al., Gene, vol. 83, pp. 15–24 (1989).

* cited by examiner

*Primary Examiner*—James Ketter
*Assistant Examiner*—Lisa Gansheroff
(74) *Attorney, Agent, or Firm*—Elias J. Lambiris; Jason I. Garbell

(57) ABSTRACT

A method for the construction of a library of recombined polynucleotides from a number of different starting single or double stranded parental DNA templates is disclosed, wherein the starting single or double stranded parental DNA templates represent discrete points in a population of genes encoding evolutionary or synthetic homologues of a peptide having homologies ranging over a broad spectrum from less than 15% to more than 80%, said population exhibiting at least one identification sequence, and whereby said genes are subjected to a gene shuffling procedure to generate shuffled mutants of said population of genes representing additional discrete points between those of said starting templates.

31 Claims, No Drawings

### METHODS OF PRODUCING POLYNUCLEOTIDE VARIANTS

CROSS-REFERENCE TO RELATED APPLICATIONS

This application is a continuation of U.S. Ser. No. 09/040,698 filed Mar. 18, 1998, now U.S. Pat. No. 6,159,688 which claims priority under 35 U.S.C. 119 of Danish applications serial no. 03006/97 filed Mar. 18, 1997, 0433/97 filed Apr. 17, 1997, and 0623/97 filed May 20, 1997, and to U.S. provisional applications No. 60/044,944 filed Apr. 25, 1997 and No. 60/050,632 filed Jun. 24, 1997, which provisional applications are incorporated herein by reference.

FIELD OF THE INVENTION

The present invention relates to optimizing DNA sequences in order to (a) improve the properties of a protein of interest by artificial generation of genetic diversity of genes encoding proteins having a biological activity of interest by the use of the so-called gene- or DNA shuffling technique to create a large library of "genes", expressing said library of genes in a suitable expression system and screening the expressed proteins in respect of specific characteristics to determine such proteins exhibiting desired properties or (b) improve the properties of regulatory elements such as promoters or terminators by generation of a library of these elements, transforming suitable hosts therewith in operable conjunction with a structural gene, expressing said structural gene and screening for desirable properties in the regulatory element.

BACKGROUND OF THE INVENTION

It is generally found that a protein performing a certain bioactivity exhibits a certain variation between genera and even between members of the same species differences may exist. This variation is of course even more outspoken at the genomic level.

This natural genetic diversity among genes coding for proteins having basically the same bioactivity has been generated in Nature over billions of years and reflects a natural optimization of the proteins coded for in respect of the environment of the organism in question.

In today's society the conditions of life are vastly removed from the natural environment and it has been found that the naturally occurring bioactive molecules are not optimized for the various uses to which they are put by mankind, especially when they are used for industrial purposes.

It has therefore been of interest to industry to identify such bioactive proteins that exhibit optimal properties in respect of the use to which it is intended.

This has for many years been done by screening of natural sources, or by use of mutagenesis. For instance, within the technical field of enzymes for use in e.g. detergents, the washing and/or dishwashing performance of e.g. naturally occurring proteases, lipases, amylases and cellulases have been improved significantly, by in vitro modifications of the enzymes.

In most cases these improvements have been obtained by site-directed mutagenesis resulting in substitution, deletion or insertion of specific amino acid residues which have been chosen either on the basis of their type or on the basis of their location in the secondary or tertiary structure of the mature enzyme (see for instance U.S. Pat. No. 4,518,584).

In this manner the preparation of novel polypeptide variants and mutants, such as novel modified enzymes with altered characteristics, e.g. specific activity, substrate specificity, thermal, pH and salt stability, pH-optimum, pI, $K_m$, $V_{max}$ etc., has successfully been performed to obtain polypeptides with improved properties.

For instance, within the technical field of enzymes the washing and/or dishwashing performance of e.g. proteases, lipases, amylases and cellulases have been improved significantly.

An alternative general approach for modifying proteins and enzymes has been based on random mutagenesis, for instance, as disclosed in U.S. Pat. No. 4,894,331 and WO 93/01285.

As it is a cumbersome and time consuming process to obtain polypeptide variants or mutants with improved functional properties a few alternative methods for rapid preparation of modified polypeptides have been suggested.

Weber et al., (1983), Nucleic Acids Research, vol. 11, 5661–5661, describes a method for modifying genes by in vivo recombination between two homologous genes. A linear DNA sequence comprising a plasmid vector flanked by a DNA sequence encoding alpha-1 human interferon in the 5'-end and a DNA sequence encoding alpha-2 human interferon in the 3'-end is constructed and transfected into a recA positive strain of E. coli. Recombinants were identified and isolated using a resistance marker.

Pompon et al., (1989), Gene 83, p. 15–24, describes a method for shuffling gene domains of mammalian cytochrome P-450 by in vivo recombination of partially homologous sequehces in Saccharomyces cerevisiae by transforming Saccharomyces cerevisiae with a linearized plasmid with filled-in ends, and a DNA fragment being partially homologous to the ends of said plasmid.

In WO 97/07205 a method is described whereby polypeptide variants are prepared by shuffling different nucleotide sequences of homologous DNA sequences by in vivo recombination using plasmid DNA as template.

U.S. Pat. No. 5,093,257 (Assignee: Genencor Int. Inc.) discloses a method for producing hybrid polypeptides by in vivo recombination. Hybrid DNA sequences are produced by forming a circular vector comprising a replication sequence, a first DNA sequence encoding the amino-terminal portion of the hybrid polypeptide, a second DNA sequence encoding the carboxy-terminal portion of said hybrid polypeptide. The circular vector is transformed into a rec positive microorganism in which the circular vector is amplified. This results in recombination of said circular vector mediated by the naturally occurring recombination mechanism of the rec positive microorganism, which include prokaryotes such as Bacillus and E. coli, and eukaryotes such as Saccharomyces cerevisiae.

One method for the shuffling of homologous DNA sequences has been described by Stemmer (Stemmer, (1994), Proc. Natl. Acad. Sci. U.S.A., Vol. 91, 10747–10751; Stemmer, (1994), Nature, vol. 370, 389–391). The method concerns shuffling homologous DNA sequences by using in vitro PCR techniques. Positive recombinant genes containing shuffled DNA sequences are selected from a DNA library based on the improved function of the expressed proteins.

The above method is also described in WO 95/22625. WO 95/22625 relates to a method for shuffling of homologous DNA sequences. An important step in the method described in WO 95/22625 is to cleave the homologous template double-stranded polynucleotide into random fragments of a desired size followed by homologously reassembling of the fragments into full-length genes.

A disadvantage inherent to the method of WO 95/22625 is, however, that the diversity generated through that method is limited due to the use of homologous gene sequences (as defined in WO 95/22625).

Another disadvantage in the method of WO 95/22625 lies in the production of the random fragments by the cleavage of the template double-stranded polynucleotide.

A further reference of interest is WO 95/17413 describing a method of gene or DNA shuffling by recombination of specific DNA sequences—so-called design elements (DE)—either by recombination of synthesized double-stranded fragments or recombination of PCR generated sequences to produce so-called functional elements (FE) comprising at least two of the design elements. According to the method described in WO 95/17413 the recombination has to be performed among design elements that have DNA sequences with sufficient sequence homology to enable hybridization of the different sequences to be recombined.

WO 95/17413 therefore also entails the disadvantage that the diversity generated is relatively limited. Furthermore the methods described are time consuming, expensive, and not suited for automation.

Despite the existence of the above methods there is still a need for better iterative in vivo recombination methods for preparing novel polypeptide variants. Such methods should also be capable of being performed in small volumes, and amenable to automation.

Furthermore, there also is a need for methods providing the possibility of being able to shuffle genes with relatively low homology.

SUMMARY OF THE INVENTION

The present invention relates to a method for the construction of a library of recombined polynucleotides from a number of different starting single or double stranded parental DNA templates, wherein said starting single or double stranded parental DNA templates represent discrete points in a population of genes encoding evolutionary or synthetic homologues of a peptide having homologies ranging over a broad spectrum from less than 15% to more than 80%, said population exhibiting at least one identification sequence, and whereby said genes are subjected to a gene shuffling procedure to generate shuffled mutants of said population of genes representing additional discrete points between those of said starting templates.

The gene shuffling procedure to be used according to the invention can be any suitable method such as those described above or a procedure as described in our co-pending patent application filed on the same date, and outlined below.

According to that procedure template shifts of newly synthesized DNA strands during in vitro DNA synthesis are utilized to achieve DNA shuffling.

In a further aspect the invention relates to a method of identifying polypeptides exhibiting improved properties in comparison to naturally occurring polypeptides of the same bioactivity, whereby a library of recombined polynucleotides produced by the above process are cloned into an appropriate vector, said vector is then transformed into a suitable host system, to be expressed into the corresponding polypeptides, said polypeptides are then screened in a suitable assay, and positive results selected.

In a still further aspect the invention relates to a method for producing a polypeptide of interest as identified in the preceding process, whereby a vector comprising a polynucleotide encoding said polypeptide is transformed into a suitable host, said host is grown to express said polypeptide, and the polypeptide recovered and purified.

Definitions

Prior to discussing this invention in further detail, the following terms will first be defined.

"Shuffling": The term "shuffling" herein means recombination of nucleotide sequence fragment(s) between two or more polynucleotides resulting in output polynucleotides (i.e. polynucleotides having been subjected to a shuffling cycle) having a number of nucleotide fragments exchanged, in comparison to the input polynucleotides (i.e. starting point polynucleotides).

"Homology of DNA sequences or polynucleotides" In the present context the degree of DNA sequence homology is determined as the degree of identity between two sequences indicating a derivation of the first sequence from the second. The homology may suitably be determined by means of computer programs known in the art, such as GAP provided in the GCG program package (Program Manual for the Wisconsin Package, version 8, August 1994, Genetics Computer Group, 575 Science Drive, Madison, Wis., U.S.A. 53711) (Needleman, S. B. and Wunsch, C. D., (1970), Journal of Molecular Biology, 48, 443–453).

"Homologous": The term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later (vide infra).

Using the computer program GAP (vide supra) with the following settings for DNA sequence comparison: GAP creation penalty of 5.0 and GAP extension penalty of 0.3, it is in the present context believed that two DNA sequences will be able to hybridize (using low stringency hybridization conditions as defined below) if they mutually exhibit a degree of identity preferably of at least 70%, more preferably at least 80%, and even more preferably at least 85%.

"heterologous": If two or more DNA sequences mutually exhibit a degree of identity which is less than above specified, they are in the present context said to be "heterologous".

"Hybridization:" Suitable experimental conditions for determining if two or more DNA sequences of interest do hybridize or not is herein defined as hybridization at low stringency as described in detail below.

Molecules to which the oligonucleotide probe hybridizes under these conditions are detected using a x-ray film or a phosphoimager.

"primer": The term "primer" used herein especially in connection with a PCR reaction is an oligonucleotide (especially a "PCR-primer") defined and constructed according to general standard specification known in the art ("PCR A practical approach" IRL Press, (1991)).

"A primer directed to a sequence:" The term "a primer directed to a sequence" means that the primer (preferably to be used in a PCR reaction) is constructed to exhibit at least 80% degree of sequence identity to the sequence part of interest, more preferably at least 90% degree of sequence identity to the sequence part of interest, which said primer consequently is "directed to". The primer is designed in order to specifically anneal at the region at a given temperature it is directed towards. Especially identity at the 3' end of the primer is essential for the function of the polymerase, i.e. the ability of a polymerase to extend the annealed primer.

"Flanking" The term "flanking" used herein in connection with DNA sequences comprised in a PCR-fragment means the outer-most partial sequences of the PCR-fragment, both in the 5' and 3' ends of the PCR fragment.

"Polypeptide" Polymers of amino acids sometimes referred to as protein. The sequence of amino acids determines the folded conformation that the polypeptide assumes, and this in turn determines biological properties such as activity. Some polypeptides consist of a single polypeptide chain (monomeric), whilst other comprise several associated polypeptides (multimeric). All enzymes and antibodies are polypeptides.

"Enzyme" A protein capable of catalysing chemical reactions. Specific types of enzymes are a) hydrolases including amylases, cellulases and other carbohydrases, proteases, and lipases, b) oxidoreductases, c) Ligases, d) Lyases, e) Isomerases, f) Transferases, etc. Of specific interest in relation to the present invention are enzymes used in detergents, such as proteases, lipases, cellulases, amylases, etc.

DETAILED DESCRIPTION OF THE INVENTION

All possible genes encoding a polypeptide of the same evolutionary origin can be seen as a very large population of DNA sequences (e.g. $\{G_{sp}\}$ the set of genes encoding a serine protease}). It has been found that the homology between the polypeptides encoded by single members of such a population may be even as small as less than 15% (the genes originating from "distant" organisms).

When searching for polypeptides suited for the various purposes that mankind has developed, it has been found difficult, if not impossible at our present level of knowledge, to conclude in a rational manner on the optimal configuration of the polypeptide in question. Therefore it was found desirable to provide a simple method of generating a sub-population of the above mentioned very large population, but representing a substantial part of the variation possible within the large population.

The object of the present invention is thus to provide a method whereby it is possible to shuffle components of genes encoding polypeptides of the same functionality, but having only low homologies.

To this end it is necessary to obtain a reasonable knowledge of the population in question, meaning having at disposal a number of individual members ( e.g. 5, 10, 15 or more members) representing as high a variation as possible. This small sub-population is then used as a starting point for generating a much larger sub-population of genes. The corresponding polypeptides of the large sub-population obtained are then displayed and screened in an appropriate manner to identify such members of the large sub-population that are optimal for the intended purpose.

It was found that the expansion of the starting sub-population to the large sub-population could be accomplished using gene shuffling methods.

Such methods as described in the literature provide means to exchange DNA fragments between genes coding for polypeptides of a reasonably high homology, typically to be above 80%, resulting in the generation of novel genes encoding polypeptides having homologies between 80% and 99%.

It was also found that in the method of the invention it was necessary as starting population to use genes encoding polypeptides that are at least from 70% to 80% homologous to at least one other gene in the starting population.

According to the invention it is thus important to start from a population or sub-set of genes which comprises intermediate sequences ranging from genes being rather similar to genes being rather dissimilar, but still having the same evolutionary origin (function). Only then a shuffling of even rather heterologous sequences is feasible. The stepwise shuffling of, first, quite homologous genes creates new species which are not contained in the starting population, and which, in the subsequent shuffling rounds, will recombine with each other and with other more heterologous genes from the starting population, and so on.

Finally, hybrids are generated in which sequence parts from very heterologous starting genes can be found. These retrieved starting genes would have never been shuffled without having the intermediate species in the starting population because of a too large "sequence space" distance.

Having this condition fulfilled it was found that it was possible to generate genes encoding novel functional polypeptides having a homology as low as the minimum degree of homology represented in the starting population. In principle the homology range in the final population may be even greater than that for the starting population.

The present invention relates in its first aspect to a method for the construction of a library of recombined polynucleotides from a number of different starting single or double stranded parental DNA templates, wherein said starting single or double stranded parental DNA templates represent discrete points in a population of genes encoding evolutionary or synthetic homologues of a peptide having homologies ranging over a broad spectrum from less than 15% to more than 80%, said population exhibiting at least one identification sequence, and whereby said genes are subjected to a gene shuffling procedure to generate shuffled mutants of said population of genes representing additional discrete points between those of said starting templates.

According to the invention it is possible to use parental DNA templates representing homologies ranging from less than 45%, 40%, 35%, 30%, 25%, 20%, or 15% to more than 80%, 85%, 90%, 95%, or 99%.

In specific embodiments at least one identification sequence is identified and primers constructed to anneal thereto. These sequences can be located anywhere on the genes.

In a preferred embodiment at leasts two identification sequences are identified. These sequences can be located at any distance from each other, but it is preferred that they are located as far as possible from each other on the genes.

According to these embodiments said identification sequences may correspond to an amino acid sequence of from 4 to 8 amino acid residues, which sequence is highly conserved among the peptides encoded by the collection of starting single or double stranded parental DNA templates, preferably from 5 to 7 amino acid residues.

It is preferred that the identification sequences are located a distance apart corresponding to the average size of the genes in said collection with a variation of up to 40%. The longer apart the sequences are the larger a part of the gene is shuffled.

However, situations may arise, where it is desired only to shuffle the sequences between identification sequences located quite close to each other.

As indicated above the gene shuffling method used in the method of the invention is of less or no significance. In principle any method will work.

Thus the methods disclosed in WO 95/22625 and WO 95/17413 are fully operable in the present invention. Details showing how these methods may be used for practising the present invention are indicated in the Examples below.

Therefore further gene shuffling methods described in cofiled patent applications are also contemplated for use in the present method.

According to one of these procedures template shifts of newly synthesized DNA strands during in vitro DNA synthesis are utilized to achieve DNA shuffling.

More specifically that method provides for the construction of a library of recombined homologous polynucleotides from a number of different starting single or double stranded parental DNA templates and primers by induced template shifts during an in vitro polynucleotide synthesis using a polymerase, whereby A. extended primers or polynucleotides are synthesized by
  a) denaturing parental double stranded DNA templates to produce single stranded templates,
  b) annealing said primers to the single stranded DNA templates,
  c) extending said primers by initiating synthesis by use of said polymerase,
  d) cause arrest of the synthesis, and
  e) denaturing the double strand to separate the extended primers from the templates,
B. a template shift is induced by
  a) isolating the newly synthesized single stranded extended primers from the templates and repeating steps A.b) to A.e) using said extended primers produced in (A) as both primers and templates, or
  b) repeating steps A.b) to A.e),
C. the above process is terminated after an appropriate number of cycles of process steps A. and B.a), A. and B.b), or combinations thereof, and
D. optionally the produced polynucleotides are amplified in a standard PCR reaction with specific primers to selectively amplify polynucleotides of interest.

In a further specific embodiment the gene shuffling is performed by the method described in our co-filed application, whereby conserved regions of heterologous DNA sequences are identified for shuffling of heterologous DNA sequences of interest having at least one conserved region comprising the following steps:

i) One or more conserved region(s) (designated "A,B,C" etc.) in two or more of the heterologous sequences are identified.
ii) Two sets of PCR primers (each set comprising a sense and an anti-sense primer) for one or more conserved region(s) identified in (i) are constructed.

In these primers, one set (named: "a"=sense primer; "a'"=anti-sense primer) is directed to a sequence region 5' (sense strain) of the conserved region (e.g. conserved region "A"), and the second set (named: "b"=sense primer; "b'"= anti-sense primer) is directed to a sequence region 3' (sense strain) of the conserved region (e.g. conserved region "A"), and the antisense primer "a'" and the sense primer "b" have a homologous sequence overlap of at least 10 base pairs (bp) within the conserved region.
iii) for one or more identified conserved region of interest in step (i) two PCR amplification reactions are performed using the heterologous DNA sequences from step (i) as templates, whereby one of the PCR reactions is using the 5' primer set identified in step (ii) (e.g. named "a", "a'") and the second PCR reaction is using the 3' primer set identified in step (ii) (e.g. named "b", "b'").
iv) The PCR fragments generated as described in step (iii) for one or more of the identified conserved region in step (i); are isolated.
v) Two or more PCR fragments isolated from step (iv) and performance of a Sequence overlap extension PCR reaction (SOE-PCR) using the isolated PCR fragments as templates are pooled.
vi) The PCR fragment(s) obtained in step (v) are isolated, whereby the isolated PCR fragment comprise numerous different shuffled sequences containing a shuffled mixture of the PCR fragments isolated in step (iv).

In specific embodiments various modifications can be made in the process of the invention. For example it is advantageous to apply a defective polymerase either an error-prone polymerase to introduce mutations in comparison to the templates, or a polymerase that will discontinue the polynucleotide synthesis prematurely to effect the arrest of the reaction.

According to a specific embodiment the peptide is a protease, especially a subtilase.

In the case of a subtilase identification sequences may be located around the aspartic acid in position 32, or the histidine in position 64 and the active serine in position 221 of subtilisin BPN'.

In a further embodiment the peptide is an amylase, especially an α-amylase.

In that case of identification sequences may be located around the Asp in position 100 and the Asp in position 328 of B. licheniformis α-amylase.

For α-amylases from Bacillus species the identification sequences may preferentially be located around Tyr in position 8 and around Ser in position 476.

In further embodiments the peptide is a lipase, or a cellulase.

In respect of cellulases, in particular cellulases from family 45 cellulases (see WO 96/29397), suitable identification sequences may be the conserved region ""Thr Arg Tyr Trp Asp Cys Cys Lys Pro/Thr" (SEQ. ID NO.1) and the conserved region ""Trp Arg Phe/Tyr Asp Trp Phe" (SEQ ID NO.2). For further details relating to those cellulase identification sequences reference is made to (PCT DK97/00216). See in particular in example 3 of (PCT DK97/00216).

In respect of cellulases, in particular cellulases from family 45 cellulases (see WO 96/29397), suitable identification sequences may be the conserved region ""Thr Arg Tyr Trp Asp Cys Cys Lys Pro/Thr" and the conserved region ""Trp Arg Phe/Tyr Asp Trp Phe". For further details relating to those cellulase identification sequences reference is made to (PCT DK97/00216). See in particular in example 3 of (PCT DK97/00216).

In respect of xylanases, in particular xylanases from family 11 xylanases, suitable identification sequences may be the conserved regions "DGGTYDIY" (SEQ. ID NO.3) and "EGYQSSG" (SEQ. ID NO.4). For further details relating to those xylanase identification sequences reference is made to (PCT DK97/00216). See in particular in example 1,2 of (PCT DK97/00216).

PCR-primers

The PCR primers are constructed according to the standard descriptions in the art. Normally they are 10–75 basepairs (bp) long. However, for the specific embodiment using random or semi-random primers the length may be substantially longer as indicated above.

PCR-reactions

If not otherwise mentioned the PCR-reaction performed according to the invention are performed according to standard protocols known in the art.

The term "Isolation of PCR fragment" is intended to cover as broad as simply an aliquot containing the PCR fragment. However preferably the PCR fragment is isolated to an extend which remove surplus of primers, nucleotides templates etc.

In an embodiment of the invention the DNA fragment(s) is(are) prepared under conditions resulting in a low, medium or high random mutagenesis frequency.

To obtain low mutagenesis frequency the DNA sequence (s) (comprising the DNA fragment(s)) may be prepared by a standard PCR amplification method (U.S. Pat. No. 4,683, 202 or Saiki et al., (1988), Science 239, 487–491).

A medium or high mutagenesis frequency may be obtained by performing the PCR amplification under conditions which increase the misincorporation of nucleotides, for instance as described by Deshler, (1992), GATA 9(4), 103–106; Leung et al., (1989), Technique, Vol. 1, No. 1, 11–15.

It is also contemplated according to the invention to combine the PCR amplification (i.e. according to this embodiment also DNA fragment mutation) with a mutagenesis step using a suitable physical or chemical mutagenizing agent, e.g., one which induces transitions, transversions, inversions, scrambling, deletions, and/or insertions.

Expressing the Recombinant Protein from the Recombinant Shuffled Sequences

Expression of the recombinant protein encoded by the shuffled sequence in step vi) of the second and third aspect of the present invention may be performed by use of standard expression vectors and corresponding expression systems known in the art.

Screening and Selection

In the context of the present invention the term "positive polypeptide variants" means resulting polypeptide variants possessing functional properties which has been improved in comparison to the polypeptides producible from the corresponding input DNA sequences. Examples, of such improved properties can be as different as e.g. enhance or lowered biological activity, increased wash performance, thermostability, oxidation stability, substrate specificity, antibiotic resistance etc.

Consequently, the screening method to be used for identifying positive variants depend on which property of the polypeptide in question it is desired to change, and in what direction the change is desired.

A number of suitable screening or selection systems to screen or select for a desired biological activity are described in the art. Examples are:

Strauberg et al. (Biotechnology 13: 669–673 (1995), describes a screening system for subtilisin variants having a Calcium-independent stability;

Bryan et al. (Proteins 1:326–334 (1986)) describes a screening assay for protease having enhanced thermal stability; and PCT-DK96/00322 describes a screening assay for lipases having an improved wash performance in washing detergents.

An embodiment of the invention comprise screening or selection of recombinant protein(s), wherein the desired biological activity is performance in dish-wash or laundry detergents. Examples of suitable dish-wash or laundry detergents are disclosed in PCT-DK96/00322 and WO 95/30011.

If the improved functional property of the polypeptide is not sufficiently good after one cycle of shuffling, the polypeptide may be subjected to another cycle.

In an embodiment of the invention wherein polynucleotides representing a number of mutations of the same gene is used as templates at least one shuffling cycle is a backcrossing cycle with the initially used DNA fragment, which may be the wild-type DNA fragment. This eliminates nonessential mutations. Non-essential mutations may also be eliminated by using wild-type DNA fragments as the initially used input DNA material.

Also contemplated to be within the invention is polypeptides having biological activity such as insulin, ACTH, glucagon, somatostatin, somatotropin, thymosin, parathyroid hormone, pituary hormones, somatomedin, erythropoietin, luteinizing hormone, chorionic gonadotropin, hypothalamic releasing factors, antidiuretic hormones, thyroid stimulating hormone, relaxin, interferon, thrombopoeitin (TPO) and prolactin.

It is also contemplated according to the invention to shuffle parental polynucleotides as indicated above originating from wild type organisms of different genera.

The starting parental DNA sequences may be any DNA sequences including wild-type DNA sequences, DNA sequences encoding variants or mutants, or modifications thereof, such as extended or elongated DNA sequences, and may also be the outcome of DNA sequences having been subjected to one or more cycles of shuffling (i.e. output DNA sequences) according to the method of the invention or any other method (e.g. any of the methods described in the prior art section), or synthetic sequences or otherwise mutagenized sequences.

When using the method of the invention the resulting recombined polynucleotides (i.e. shuffled DNA sequences), have had a number of nucleotide fragments exchanged. This results in replacement of at least one amino acid within the polypeptide variant, if comparing it with the parent polypeptide. It is to be understood that also silent exchanges are contemplated (i.e. nucleotide exchange which does not result in changes in the amino acid sequence).

Materials and Methods

EXAMPLES

Example 1

Shuffling of a Pool/Population of Evolutionary Homoloques Originating from Bacterial Hosts A population of subtilase-encoding genes or parts of such genes are generated through isolation or by synthesis. Sources for the genes may be as described in Siezen et al. *Protein Engineering* 4 1991 719–737. The population may also comprise genes encoding the pre-pro subtilases as defined in GenBank entries A13050_1, D26542, A22550, Swiss-Prot entry SUBT_BACAM P00782, and PD498 (Patent Application No. WO 96/34963) with homologies (similarities) ranging from 32% to 64% as calculated by the MEGALIGN software from DNASTAR Inc. (WI 53715, USA) using the CLUSTAL Method.

The substrates used in the shuffling reaction are represented by linear double stranded DNA generated by PCR amplification using primers located at/directed towards the ends of the DNA to be shuffled. In this instance the primers can conveniently be constructed using the sequences surrounding the histidine in pos 64 of subtilisin BPN' and the serine in position 221 of subtilisin BPN'. The template for this PCR can either be plasmids containing cloned protease genes or chromosomal DNA extracted from bacterial strains e.g. protease secreting bacteria isolated from soil. The substrate will typically be generated separately for all the templates and pooled before the shuffling reaction.

The substrates are fragmented e.g. by DNAse I treatment or shearing by sonication as described in WO 95/22625. The generated fragments are separated according to size by agarose gel electrophoresis and generated fragment of the desired size, e.g. from 10 to 50 bp. or from 30 to 100 bp, or from 50 to 150 bp, or from 100 to 200 bp are purified from the gel.

These fragments are reassembled by PCR as described in WO95/22625. Optionally, correctly assembled DNA fragments are amplified by subjecting the product from the assembly reaction to another PCR including two primers able to anneal to the ends of correctly assembled fragments. The resulting fragments can be cloned into suitable expression plasmids, and subsequently screened for a specific property, such as thermostability using assays well known in the art.

What is claimed is:

1. A method for generating recombined polynucleotides encoding functionally similar polypeptides, the method comprising:
   (a) providing a starting population of polynucleotides encoding functionally similar polypeptides, wherein said population comprises at least two such polynucleotides that have a homology of less than 45%, and wherein each polynucleotide of the population is at least 70% homologous to at least one other polynucleotide of the population;

(b) shuffling said population under conditions that allow recombined polynucleotides to be generated from parental polynucleotides that have at least 70% homology, wherein recombined polynucleotides encoding functionally similar polypeptides are generated.

2. The method of claim 1, wherein said step (b) is repeated in one or more subsequent shuffling rounds.

3. The method of claim 1, further comprising (c) cloning the recombined polynucleotides generated in said step (b)

into a vector, transforming a host cell, and expressing the recombined polynucleotides.

4. The method of claim 3, further comprising (d) screening the expressed polypeptides for a recombined polypeptide of interest exhibiting a desired changed property relative to a nonrecombined polypeptide of interest.

5. The method of claim 1, wherein one or more conserved region(s) is identified in at least two polynucleotides comprised in the population of said step (a), and wherein said step (b) is performed using at least one set of PCR-primers directed to said conserved region(s).

6. The method of claim 5, wherein two conserved regions are identified.

7. The method of claim 6, wherein said two conserved regions correspond to amino acid sequences of from 4 to 8 amino acid residues.

8. The method of claim 6, wherein said two conserved regions correspond to amino acid sequences of from 5 to 7 amino acid residues.

9. The method of claim 5, wherein said at least one set of primers is two or more sets.

10. A method of identifying a recombined polypeptide of interest exhibiting a desired changed property relative to a nonrecombined polypeptide of interest, the method comprising:
(a) providing a starting population of polynucleotides encoding functionally similar polypeptides, wherein said population comprises at least two such polynucleotides that have a homology of less than 45%, and wherein each polynucleotide of the population is at least 70% homologous to at least one other polynucleotide of the population;
(b) shuffling said population under conditions that allow recombined polynucleotides to be generated from parental polynucleotides that have at least 70% homology, wherein recombined polynucleotides encoding functionally similar polypeptides are generated;
(c) expressing recombined polynucleotides generated by said step (b);
(d) screening the expressed polypeptides; and
(e) selecting an expressed recombined polypeptide of interest for a desired changed property relative to the nonrecombined polypeptide of interest.

11. The method of claim 10, wherein the polypeptide of interest is an enzyme.

12. The method of claim 10, wherein the polypeptide of interest is a protease.

13. The method of claim 10, wherein the polypeptide of interest is a subtilisin or subtilase.

14. The method of claim 10, wherein the polypeptide of interest is a subtilisin obtained from Bacillus.

15. The method of claim 10, wherein the polypeptide of interest is a subtilisin; and wherein said step (b) further comprises
(i) identifying two conserved regions in at least two polynucleotides encoding subtilisins, wherein said two conserved regions are respectively located around positions corresponding to position 64 and position 221 in the encoded subtilisins, according to the numbering of positions 64 (His) and 221 (Ser) in subtilisin BPN'; and
(ii) performing said shuffling using at least one set of PCR-primers directed to said two conserved regions.

16. The method of claim 10, wherein the polypeptide of interest is an amylase.

17. The method of claim 10, wherein the polypeptide of interest is an α-amylase.

18. The method of claim 10, wherein the polypeptide of interest is an α-amylase obtained from Bacillus licheniformis.

19. The method of claim 10, wherein the polypeptide of interest is an α-amylase, and wherein said step (b) further comprises:
(i) identifying two conserved regions in at least two polynucleotides encoding α-amylases, wherein said two conserved regions are respectively located around positions corresponding to positions 100 (Asp) and position 328 (Asp) in Bacillus licheniformis;
(ii) performing said shuffling using at least one set of PCR-primers directed to said two conserved regions.

20. The method of claim 10, wherein the polypeptide of interest is an α-amylase, and wherein said step (b) further comprises:
(i) identifying two conserved regions in at least two polynucleotides encoding said α-amylases, wherein said two conserved regions respectively are located around positions corresponding to positions 8 (Tyr) and 476 (Ser) in Bacillus licheniformis; and
(ii) performing said shuffling using at least one set of PCR-primers directed to said two conserved regions.

21. The method of claim 10, wherein the polypeptide of interest is a lipase.

22. The method of claim 10, wherein the polypeptide of interest is a lipase obtained from Pseudomonas glumae.

23. The method of claim 10, wherein the polypeptide of interest is a lipase, and wherein said step (b) further comprises:
(i) identifying two conserved regions in at least two polynucleotides encoding lipases, wherein said conserved regions are respectively located around positions corresponding to positions 10 (Pro) and 285 (His) in Pseudomonas glumae; and
(ii) performing said shuffling using at least one set of PCR-primers directed to said two conserved regions.

24. The method of claim 10, wherein the polypeptide of interest is a cellulase.

25. The method of claim 10, wherein the polypeptide of interest is a family 45 cellulase.

26. The method of claim 10, wherein the polypeptide of interest is a family 45 cellulase, and wherein said step (b) further comprises:
(i) identifying two conserved regions in at least two polynucleotides encoding cellulases, wherein the conserved regions are respectively located around positions corresponding to the conserved regions Thr-Arg-Tyr-Trp-Asp-Cys-Cys-Lys-Pro/Thr (SEQ ID NO:1) and Trp-Arg-Phe/Tyr-Asp-Trp-Phe (SEQ ID NO:2) in the encoded cellulases; and
(ii) performing said shuffling using at least one set of PCR-primers directed to said two conserved regions.

27. The method of claim 10, wherein the polypeptide of interest is a xylanase.

28. The method of claim 10, wherein the polypeptide of interest is a family 11 xylanase.

29. The method of claim 10, wherein the polypeptide of interest is a family 11 xylanase, and wherein said step (b) further comprises:
(i) identifying two conserved regions in at least two polynucleotides encoding xylanases, wherein said two conserved regions are respectively located around positions corresponding to the conserved regions DGGTYDIY (SEQ ID NO:3) and EGYQSSG (SEQ ID NO:4) in the encoded xylanases; and (ii) the shuffling is performed using at least one set of PCR-primers directed to the conserved regions.

30. The method of claim 10, wherein the polypeptide of interest is an α-amylase from Bacillus species.

31. The method of claim 10, wherein the polypeptide of interest is a lipase obtained from Pseudomonas species.

* * * * *

```
                        SEQUENCE LISTING

<160> NUMBER OF SEQ ID NOS: 4

<210> SEQ ID NO 1
<211> LENGTH: 9
<212> TYPE: PRT
<213> ORGANISM: Myceliophthora
<220> FEATURE:
<221> NAME/KEY: MISC_FEATURE
<222> LOCATION: (9)..(9)
<223> OTHER INFORMATION: Xaa in position 9 is Pro or Thr

<400> SEQUENCE: 1

Thr Arg Tyr Trp Asp Cys Cys Lys Xaa
1               5

<210> SEQ ID NO 2
<211> LENGTH: 6
<212> TYPE: PRT
<213> ORGANISM: Myceliophthora
<220> FEATURE:
<221> NAME/KEY: misc_feature
<222> LOCATION: (3)..(3)
<223> OTHER INFORMATION: Xaa in position 3 is Phe or Tyr

<400> SEQUENCE: 2

Tyr Arg Xaa Asp Trp Phe
1               5

<210> SEQ ID NO 3
<211> LENGTH: 8
<212> TYPE: PRT
<213> ORGANISM: Bacillus sp.

<400> SEQUENCE: 3

Asp Gly Gly Thr Tyr Asp Ile Tyr
1               5

<210> SEQ ID NO 4
<211> LENGTH: 7
<212> TYPE: PRT
<213> ORGANISM: Bacillus sp.

<400> SEQUENCE: 4

Glu Gly Tyr Gln Ser Ser Gly
1               5
```